United States Patent [19]

Jinno et al.

[11] Patent Number: 5,734,067
[45] Date of Patent: Mar. 31, 1998

[54] ANTI-OXIDATIVE TRICYCLIC, CONDENSED HETEROCYCLIC COMPOUND

[75] Inventors: Shuji Jinno; Yasuyo Kogure; Hiroyuki Onuki; Takaaki Okita, all of Tokyo, Japan

[73] Assignee: Nippon Suisan Kaisha, Ltd., Japan

[21] Appl. No.: 809,001

[22] PCT Filed: Sep. 28, 1995

[86] PCT No.: PCT/JP95/01975

§ 371 Date: Mar. 4, 1997

§ 102(e) Date: Mar. 4, 1997

[87] PCT Pub. No.: WO96/10021

PCT Pub. Date: Apr. 4, 1996

[30] Foreign Application Priority Data

Sep. 28, 1994 [JP] Japan .................. 6-258781
Jan. 30, 1995 [JP] Japan .................. 7-033178

[51] Int. Cl.[6] .................. C07D 313/14
[52] U.S. Cl. .................. 549/349; 549/12
[58] Field of Search .................. 549/349, 12

*Primary Examiner*—Amelia Averill Owens
*Attorney, Agent, or Firm*—Lorusso & Loud

[57] ABSTRACT

Providing a novel tricyclic, condensed heterocyclic compound having an anti-oxidative action and being promising for use in pharmaceutical agents, cosmetics, chemical products and the like. By chemical synthesis, a novel anti-oxidative, tricyclic, condensed heterocyclic compound represented by the following formula:

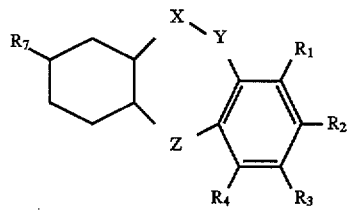

(wherein X—Y represents $CH_2$—C=O, $CH_2$—$CH_2$ or CH=CH; Z represents O, S, or S=O; $R_1$ to $R_8$ represent independently those selected from the group consisting of hydrogen atom, a hydroxyl group, a halogen group, a lower alkyl group, a lower alkoxyl group, a lower alkyl ketone group and $CF_3$; and at least two of $R_1$ to $R_4$ are hydroxyl groups); and the salts thereof are provided. The compound has an anti-oxidative activity at the same degree as or higher than the activity of α-tocopherol, so the compound is promising as a therapeutic drug for a variety of diseases, such as cancer, arteriosclerosis, or liver diseases, in which it is believed that biological lipid peroxides may be involved.

1 Claim, No Drawings

ANTI-OXIDATIVE TRICYCLIC, CONDENSED HETEROCYCLIC COMPOUND

This application is a 371 of PCT/JP95/01975 filed Sep. 28, 1995.

TECHNICAL FIELD OF THE INVENTION

The present invention relates to a novel tricyclic, condensed heterocyclic compound. The novel tricyclic, condensed heterocyclic compound in accordance with the present invention is a useful substance with an anti-oxidant action.

BACKGROUND ART

The relation between phenomena such as cancer, arteriosclerosis and aging and biological oxidative reaction has been remarked in recent years, and therefore, attention has been drawn increasingly toward anti-oxidative agents as substances capable of controlling the biological oxidizing mechanism.

The present inventors have extracted dibenzoxepin derivatives from bakery's yeast and have then found that the derivatives belong to a group of substances with an anti-oxidant action. The applicant has already filed the application thereof (Japanese Unexamined Patent Publication No. Hei 5-153990 (1993)). The application describes clearly that the dibenzoxepin derivatives represented by the following formula (1):

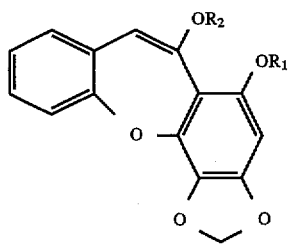

Formula (1)

(wherein $R_1$ represents hydrogen atom or an acyl group; and $R_2$ represents an alkyl group) has an anti-oxidant action.

DISCLOSURE OF THE INVENTION

Focusing attention to the finding that the dibenzoxepin derivatives described in the Unexamined Patent Publication No. Hei 5-153990 have an anti-oxidant action, the present inventors have synthesized the intermediates and derivatives thereof by organic synthesis, to investigate the properties of the resulting compounds. Then, the inventors have found the following new anti-oxidative compounds.

The present invention is to provide a novel anti-oxidative, tricyclic, condensed heterocyclic compound represented by the following formula (2):

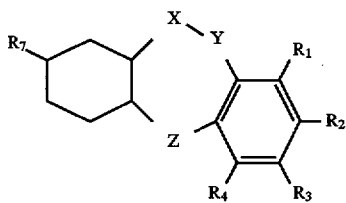

Formula (2)

(wherein X—Y represents $CH_2$—C=O(provided that X is $CH_2$ and Y is C=O), $CH_2$—$CH_2$ or CH=CH; Z represents O, S, or S=O; $R_1$ to $R_8$ represent independently those selected from the group consisting of hydrogen atom, a hydroxyl group, a halogen group, a lower alkyl group, a lower alkoxyl group, a lower alkyl ketone group and $CF_3$; and at least two of $R_1$ to $R_4$ are hydroxyl groups) and the salts thereof.

In accordance with the present invention, the term "lower alkyl group" means a linear or branched group with one up to 8 carbon atoms. In accordance with the present invention, the term "lower alkoxyl group" means —O— lower alkyl. In accordance with the present invention, the term "lower alkyl ketone group" means —(C=O)— lower alkyl. The salts of the inventive compound mean the pharmaceutically acceptable salts thereof, including for example the sodium salt, potassium salt, calcium salt, ammonium salt and aluminium salt thereof.

The novel tricyclic, condensed heterocyclic compound represented by the formula (2) in accordance with the present invention is a novel compound produced by chemical synthesis, having an anti-oxidizing activity and useful as a chemical substance for use in pharmaceutical agents, cosmetics, chemical products and the like.

It has been confirmed that the novel tricyclic, condensed heterocyclic compound of the present invention has an outstanding action of inhibiting lipid peroxides with low toxicity. Thus, the novel tricyclic, condensed heterocyclic compound of the present invention is useful as a therapeutic agent for a variety of diseases for which it is believed that lipid peroxides in organisms may be responsible, for example, cancer, arteriosclerotic disorders and liver disorders. For this purpose, the compound of the present invention may be formulated into a variety of formulations produced by the conventional pharmaceutical techniques, such as oral agents including powders, granules, tablets, sugar-coated agents, ampoules, and capsules; subcutaneous agents; intramuscular agents; intravenous agents; or suppositories. For such formulations, routine additives such as fillers, binders, disintegrators, pH adjusting agents and dissolving agents may be used.

The dose of the novel tricyclic, condensed heterocyclic compound of the present invention varies depending on the age, disease and conditions of a patient to be treated, but 10 to 5000 mg/day may generally be administered in a single dose or in several doses to an adult patient.

The novel tricyclic, condensed heterocyclic compound represented by the formula (2) of the present invention and a method for producing the compound are shown hereinafter by way of examples, but the invention is not limited to these examples.

BEST MODES FOR CARRYING OUT THE INVENTION

[EXAMPLE 1]

Production of 6,9-dihydroxy-7-methoxy-10,11-dihydrodibenz[b,f]oxepin-10-one (Compound 1)

Step 1

5-Bromovaniline (25 g) was suspended in anhydrous methylene chloride (700 ml), followed by addition of m-chloroperbenzoic acid (32 g; purity of 70%), and the resulting mixture was heated under stirring at 50° C. for 16 hours. After evaporating the solvent under reduced pressure, the residue was dissolved in ethyl acetate (700 ml), followed by washing in an aqueous saturated sodium hydrogen carbonate solution and in water, and further in a saturated sodium chloride solution, and drying over anhydrous magnesium sulfate to distill off the solvents under reduced pressure. To the resulting residue were added dioxane (76 ml) and an aqueous 3N sodium hydroxide solution (76 ml), followed by stirring at room temperature for 30 minutes. The resulting mixture was adjusted to acidity with dilute hydrochloric acid, followed by extraction in ethyl acetate three times. Washing the organic phase in water and continuously in a saturated sodium chloride solution and drying the phase over anhydrous magnesium sulfate to distill off the solvents under reduced pressure, the resulting residue was purified by silica gel column chromatography (developing solvent: hexane:ethyl acetate=1:1), to recover 2-bromo-6-methoxy-1,4-hydroquinone (15 g; yield of 63%). By $^1$H-NMR (90 MHz, CDCl$_3$), the compound has the peaks shown below.

δ(ppm) 3.87 (3H, s, OCH$_3$) 4.61 (1H, s, OH) 5.48 (1H, s, OH) 6.41(1H, d, J=2.8 Hz, Ar—H) 6.58 (1H, d, J=2.8 H z, Ar—H)

Step 2

2-Bromo-6-methoxy-1,4-hydroquinone (15 g) produced in the step 1 was dissolved in acetonitrile (400 ml), followed by addition of ammonium cerium (IV) nitrate (56.4 g) and stirring at room temperature for 20 minutes. After distilling off the solvent under reduced pressure, water and ethyl acetate were added to the residue for distribution. The ethyl acetate phase was washed in water and then in a saturated sodium chloride solution and dried over anhydrous magnesium sulfate, and after distilling off the solvents under reduced pressure, 2-bromo-6-methoxy-1,4-benzoquinone (14.7 g; yield of 99%) was recovered. By $^1$H-NMR (90 MHz, CDCl$_3$), the compound has the peaks shown below.

δ(ppm) 3.86 (3H, s, OCH$_3$) 5.96 (1H, d, J=2.3 Hz, Ar—H) 7.21 (1H, d, J=2.3 Hz, Ar—H)

Step 3

To distilled 2-allylphenol (8.4 ml) were added N,N-dimethylformamide (240 ml) and cesium carbonate (42 g), followed by further dropwise addition of 2-bromo-6-methoxy-1,4-benzoquinone (9.3 g) produced in the step 2, which was preliminarily dissolved in N,N-dimethylformamide (180 ml), and the resulting mixture was stirred at room temperature for 30 minutes. The reaction solution was diluted with ethyl acetate, washed in water and subsequently in a saturated sodium chloride solution, and dried over anhydrous magnesium sulfate, to distill off the solvents under reduced pressure. The resulting residue was purified by silica gel column chromatography (developing solvent: hexane:ethyl acetate=1:1), to recover 2-(2-allylphenoxy)6-methoxy 1,4-benzoquinone (8.4 g; yield of 68%). By $^1$H-NMR (90 MHz, CDCl$_3$), the compound has the peaks shown below.

δ(ppm) 3.29 (2H, d, J=6.6 Hz, Ar—CH$_2$) 3.86 (3H, s, OCH$_3$) 4.9–5.2 (2H, m, —CH=CH$_2$) 5.55 (1H, d, J=2.1 Hz, Ar—H) 5.8–6.1 (1H, m, —CH=CH$_2$) 5.81 (1H, d, J=2.1 Hz, Ar—H) 6.9–7.3 (4H, m, Ar—H)

Step 4

2-(2-Allylphenoxy)6-methoxy-1,4-benzoquinone (8.4 g) produced in the step 3 was dissolved in ethanol (200 ml), followed by addition of ascorbic acid (30 g) preliminarily dissolved in water (100 ml), and the resulting mixture was stirred at room temperature until the color was eliminated. After distilling off the solvents under reduced pressure, ethyl acetate extraction, washing of the organic phase in water and subsequently in a saturated sodium chloride solution, drying of the organic phase over anhydrous magnesium sulfate and subsequent distillation of the solvents under reduced pressure yielded 2-(2-allylphenoxy)6-methoxy-1,4-hydroquinone (8.5 g; yield of 100%). By $^1$H-NMR (90 MHz, CDCl$_3$), the compound has the peaks shown below.

δ(ppm) 3.44 (2H, d, J=6.6 Hz, Ar—CH$_2$) 3.88 (3H, s, OCH$_3$) 4.60 (1H, s, OH) 4.9–5.2 (2H, m, —CH=CH$_2$) 5.16 (1H, s, OH) 5.8–6.1 (1H, m, —CH=CH$_2$) 5.93 (1H, d, J=2.8 Hz, Ar—H) 6.24 (1H, d, J=2.8 Hz, Ar—H) 6.9–7.3 (4H, m, Ar—H)

Step 5

To 2-(2-allylphenoxy)6-methoxy-1,4-hydroquinone (8.5 g) produced in the step 4 were added pyridine (50 ml) and acetic anhydride (20 ml), for subsequent stirring at room temperature for one hour, prior to dilution with ethyl acetate, and the resulting solution was washed in dilute hydrochloric acid and in water, and subsequently in a saturated sodium chloride solution and dried over anhydrous magnesium sulfate. Then, the solvents were distilled off under reduced pressure. The resulting residue was purified by silica gel column chromatography (developing solvent: hexane:ethyl acetate=2:1), to recover 2-(2-allylphenoxy)1,4-diacetoxy-6-methoxybenzene (10.6 g; yield of 96%). By $^1$H-NMR (90 MHz, CDCl$_3$), the compound has the peaks shown below.

δ(ppm) 2.23 (3H, s, COCH$_3$) 2.23 (3H, s, COCH$_3$) 3.36 (2H, d, J=6.6 Hz, Ar—CH$_2$) 3.82 (3H, s, OCH$_3$) 4.9–5.2 (2H, m, —CH=CH$_2$) 5.8–6.1 (1H, m, —CH=CH$_2$) 6.14 (1H, d, J=2.4 Hz, Ar—H) 6.45 (1H, d, J=2.4 Hz, Ar—H) 6.9–7.3 (4H, m, Ar—H)

Step 6

2-(2-Allylphenoxy)1,4-diacetoxy-6-methoxybenzene (10.6 g) produced in the step 5 was dissolved in methylene chloride (175 ml), methanol (175 ml) and acetic acid (20 ml), prior to stirring at −78° C. for 20 minutes. After bubbling ozone gas into the resulting solution under stirring for 3 hours, it was confirmed that the solution turned blue. Subsequently, dimethyl sulfide (11 ml) was added to the solution, followed by stirring until the temperature of the solution elevated to room temperature. After distilling off the solvents under reduced pressure, the residue was purified by silica gel column chromatography (developing solvent: hexane:ethyl acetate=2:3), to yield 2-(2,5-diacetoxy-3-methoxyphenoxy)benzyl aldehyde (8.6 g; yield of 80%). By $^1$H-NMR (90 MHz, CDCl$_3$), the compound has the peaks shown below.

δ(ppm) 2.23 (3H, s, COCH$_3$) 2.23 (3H, s, COCH$_3$) 3.74 (2H, d, J=1.5 Hz, Ar—CH$_2$) 3.84 (3H, s, OCH$_3$) 6.21 (1H, d, J=2.4 Hz, AR—H) 6.51 (1H, d, J=2.4 Hz, Ar—H) 6.9–7.3 (4H, m, Ar—H) 9.72 (1H, t, J=1.5 Hz, CHO)

Step 7

2-(2,5-Diacetoxy-3-methoxyphenoxyl)benzyl aldehyde (8.6 g) produced in the step 6 was dissolved in a mixture solvent (484 ml) comprising tertiary butanol and 2-methyl-2-butene (4:1), followed by addition of sodium hypochlorite (8.2 g) and sodium dihydrogen phosphate (8.2 g), both dissolved in water (156 ml), prior to stirring at room temperature for one hour. The reaction solution was partitioned with ethyl acetate and water, and the resulting organic phase was washed in water and in a saturated sodium chloride solution and dried over anhydrous magnesium sulfate, and then, the solvents were distilled off under reduced pressure. To the residue was added methane sulfonic acid (120 ml), followed by stirring at room temperature for 7 days, and the resulting solution was then diluted with ethyl acetate, washed in water and in a saturated sodium chloride solution, and dried over anhydrous magnesium sulfate to distill off the solvents. The resulting residue was purified by silica gel column chromatography (developing solvent: hexane:ethyl acetate=2:3) and recrystallized in hexane and ethyl acetate, to recover 6,9-dihydroxy-7-methoxy-10,11-dihydrodibenz[b,f]oxepin-10-one (Compound 1) represented by the following formula (3) in yellow needle crystal (4.6 g; yield of 70%).

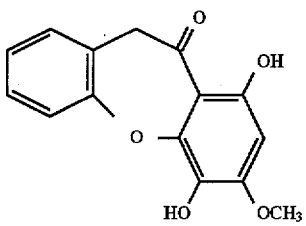

Formula (3)

The compound 1 has a melting point of 220.5° to 222.0° C. By ¹H-NMR (90 MHz, CDCl₃), the compound 1 has the peaks shown below.

δ(ppm) 3.94 (3H, s, OCH₃) 4.11 (2H, s, Ar—CH₂) 5.49(1H, s, OH) 6.28 (1H, s, Ar—H) 7.2–7.5 (4H, m, Ar—H) 12.67 (1H, s, OH)

[EXAMPLE 2]

Production of 6,7,9-trihydroxy-10,11-dihydrodibenz[b,f]oxepin-10-one (Compound 2)

0.39 g of the Compound 1 produced in Example 1 was placed in a pressure-resistant reaction vessel, followed by addition of pyridine hydrochloride salt (4 g), and stirring at 200° C. for 1.5 hours. The resulting solution was partitioned with ethyl acetate and water, and the organic phase was washed in dilute hydrochloric acid, in water and in a saturated sodium chloride solution, and dried over anhydrous magnesium sulfate to distill off the solvents under reduced pressure. The resulting residue was purified by silica gel column chromatography (developing solvent: ether) and recrystallized in hexane and ethyl acetate, to recover 6,7,9-trihydroxy-10,11-dihydrodibenz[b,f]oxepin-10-one (Compound 2) represented by the following formula (4) in brown plate crystal (285 mg; yield of 77%).

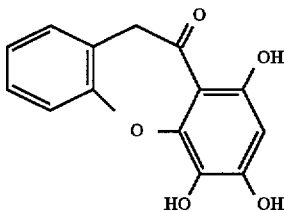

Formula (4)

The compound 2 has a melting point of 224.5° to 226.5° C. By ¹H-NMR (90 MHz, DMSO-d₆), the Compound 2 has the peaks shown below.

δ(ppm) 4.10 (2H, s, Ar—CH₂) 6.11 (1H, s, Ar—H) 7.1–7.6 (4H, m, Ar—H) 12.62 (1H, s, OH)

[EXAMPLE 3]

Production of 6,9-dihydroxy-7-methoxy-4-methyl-10,11-dihydrodibenz[b,f]oxepin-10-one (Compound 3)

The same procedures as in the steps 1 to 7 of Example 1 were carried out except for the use of 2-allyl-6-methylphenol in place of 2-allylphenol in the step 3 of Example 1, to recover 6,9-dihydroxy-7-methoxy-4-methyl-10,11-dihydrodibenz[b,f]oxepin-10-one (Compound 3) represented by the following formula (5) in pale yellow needle crystal.

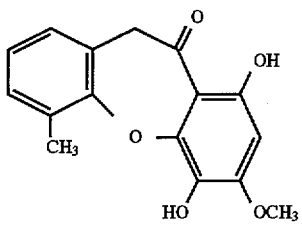

Formula (5)

The Compound 3 has a melting point of 239.7° to 241.5° C. By ¹H-NMR (90 MHz, CDCl₃), the Compound 3 has the peaks shown below.

δ(ppm) 2.44 (3H, s, CH₃) 3.88 (3H, s, OCH₃) 4.08 (2H, s, Ar—CH₂) 6.38 (1H, s, Ar—H) 7.0–7.3 (3H, m, Ar—H) 8.69 (1H, brs, OH) 12.72 (1H, s, OH)

[EXAMPLE 4]

Production of 4-methyl-6,7,9-trihydroxy-10,11-dihydrodibenz[b,f]oxepin-10-one (Compound 4)

The same procedures as in the steps 1 to 7 of Example 1 and in Example 2 were carried out except for the use of 2-allyl-6-methylphenol in place of 2-allylphenol in the step 3 of Example 1, to recover 4-methyl-6,7,9-trihydroxy-10,11-dihydrodibenz[b,f]oxepin-10-one (Compound 4) represented by the following formula (6) in mud yellow plate crystal.

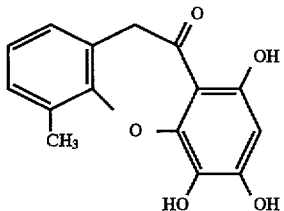

Formula (6)

The Compound 4 has a melting point of 259.6° to 260.8° C. By ¹H-NMR (90 MHz, DMSO-d₆), the Compound 4 has the peaks shown below.

δ(ppm) 2.46 (3H, s, CH₃) 4.06 (2H, s, Ar—CH₂) 6.16 (1H, s, Ar—H) 7.0–7.3 (3H, m, Ar—H) 12.65 (1H, s, OH)

[EXAMPLE 5]

Production of 6,9-dihydroxy-4,7-dimethoxy-10,11-dihydrodibenz [b,f]oxepin-10-one (Compound 5)

The same procedures as in the steps 1 to 7 of Example 1 were carried out except for the use of 2-allyl-6-methoxyphenol in place of 2-allylphenol in the step 3 of Example 1, to recover 6,9-dihydroxy-4,7-dimethoxy-10,11-dihydrodibenz[b,f]oxepin-10-one (Compound 5) represented by the following formula (7) in yellow needle crystal.

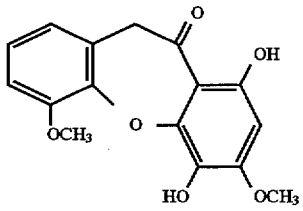

Formula (7)

The Compound 5 has a melting point of 227.8° to 229.8° C. By ¹H-NMR (90 MHz, CDCl₃), the Compound 5 has the peaks shown below.

δ(ppm) 3.92 (3H, s, OCH₃) 3.95 (3H, s, OCH₃) 4.14 (2H, s, Ar—CH₂) 6.28 (1H, s, Ar—H) 6.8–7.2 (3H, m, Ar—H) 12.59 (1H, s, OH)

[EXAMPLE 6]

Production of 4,6,7,9-tetrahydroxy-10,11-dihydrodibenz[b,f]oxepin-10-one (Compound 6)

The same procedures as in the steps 1 to 7 of Example 1 and in Example 2 were carried out except for the use of 2-allyl-6-methoxyphenol in place of 2-allylphenol in the step 3 of Example 1, to recover 4,6,7,9-tetrahydroxy-10,11-dihydrodibenz [b,f]oxepin-10-one (Compound 6) represented by the following formula (8) in mud yellow irregular-shape crystal.

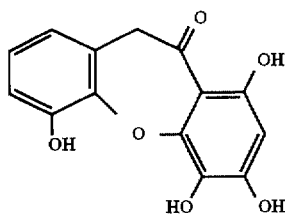

Formula (8)

The Compound 6 has a melting point of 235.4° to 236.7° C. By ¹H-NMR (90 MHz, DMSO-d₆), the Compound 6 has the peaks shown below.

δ(ppm) 4.10 (2H, s, Ar—CH₂) 6.16 (1H, s, Ar—H) 6.8–7.1 (3H, m, Ar—H) 12.54 (1H, s, OH)

[EXAMPLE 7]

Production of 6,9-dihydroxy-10,11-dihydrodibenz[b,f]oxepin-10-one (Compound 7)

The same procedures as in the steps 1 to 7 of Example 1 were carried out except for the use of 2-chloro-4-hydroxybenzaldehyde in place of 5-bromovaniline in the step 1 of Example 1, to recover 6,9-dihydroxy-10,11-dihydrodibenz[b,f]oxepin-10-one (Compound 7) represented by the following formula (9) in yellow plate crystal.

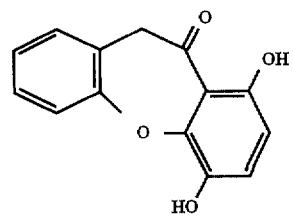

Formula (9)

The Compound 7 has a melting point of 182.5° to 184.0° C. By ¹H-NMR (90 MHz, CDCl₃), the Compound 7 has the peaks shown below.

δ(ppm) 4.15 (2H, s, Ar—CH₂) 5.81 (1H, brs, OH) 6.67 (1H, d, J=9.1 Hz, Ar—H) 7.22 (1H, d, J=9.1 Hz, Ar—H) 7.2–7.4 (4H, m, Ar—H)
11.92 (1H, s, OH)

[EXAMPLE 8]

Production of 6,7-dihydroxy-10,11-dihydrodibenz[b, f]oxepin-10-one (Compound 8)

Step 1

Amyl alcohol (44 ml) was added to 2,3-dimethoxyphenol (5 g), 2'-bromoacetophenone (7 g), potassium carbonate (6.7 g) and copper acetate (1.1 g), followed by heating and stirring at 150° C. for 8 hours for reacting them together. To the reaction solution was added ethyl acetate (300 ml), and the resulting solution was washed in dilute hydrochloric acid, in water, and in a saturated sodium chloride solution, and dried over anhydrous magnesium sulfate, and the solvents therein were distilled off under reduced pressure. The residue was purified by silica gel column chromatography (developing solvent: hexane:ethyl acetate=8:1), to recover 2-(2,3-dimethoxyphenoxy)acetophenone (7.6 g; yield of 87%). By ¹H-NMR (90 MHz, CDCl₃), the compound has the peaks shown below.

δ(ppm) 2.73 (3H, s, CH₃) 3.78 (3H, s, OCH₃) 3.91 (3H, s, OCH₃) 6.6–7.9 (7H, m, Ar—H)

Step 2

To 2-(2,3-dimethoxyphenoxy)acetophenone (7.6 g) produced in the step 1 were added sulfur (2.7 g) and morpholine (3.7 ml), followed by heating and stirring at 150° C. for 10 minutes and subsequent addition of p-toluenesulfonic acid (0.15 g) for 8-hr heating at 150° C. under stirring. Ethyl acetate (300 ml) and dilute hydrochloric acid (100 ml) were added to the resulting mixture for partition. The organic phase was washed in water and then in a saturated sodium chloride solution and dried over anhydrous magnesium sulfate, and the solvents were distilled off under reduced pressure. To the resulting residue were added conc. hydrochloric acid (100 ml) and conc. acetic acid (100 ml), prior to stirring at 150° C. for 8 hours, followed by addition of ethyl acetate (300 ml) and water (100 ml), partition with the developing solvent, separation of the organic phase, and washing of the organic phase in water and in a saturated sodium chloride solution. The resulting matter was dried over anhydrous magnesium sulfate, to distill off the solvents therein under reduced pressure. To the resulting residue was added methanesulfonic acid (100 ml), for stirring at room temperature for 3 days, followed by addition of ethyl acetate (300 ml) and washing in water and in a saturated sodium chloride solution. Subsequently, the resulting matter was dried over anhydrous magnesium sulfate, and the solvents were distilled off under reduced pressure. The resulting residue was purified by silica gel column chromatography (developing solvent: hexane:ethyl acetate=5:1), to recover 6,7-dimethoxy-10,11-dihydrodibenz[b,f]oxepin-10-one (2.8 g; yield of 37%). By ¹H-NMR (90 MHz, CDCl₃), the compound has the peaks shown below.

δ(ppm) 3.94 (3H, s, OCH₃) 4.04 (3H, s, OCH₃) 4.08 (2H, s, Ar—CH₂) 6.77 (1H, d, J=9.2 Hz, Ar—H) 7.2–7.4 (4H, m, Ar—H) 7.83 (1H, d, J=9.2 Hz, Ar—H)

Step 3

6,7-Dimethoxy-10,11-dihydrodibenz[b,f]oxepin-10-one (2.8 g) produced in the step 2 was placed in a pressure-resistant reaction vessel, followed by addition of pyridine hydrochloride salt (28 g), heating and stirring at 200° C. for 1.5 hours, and partition with ethyl acetate and water. The resulting organic phase was washed in dilute hydrochloric acid and in water and subsequently in a saturated sodium chloride solution, and dried over anhydrous magnesium sulfate, and the solvents were distilled off under reduced pressure. The resulting residue was purified by silica gel column chromatography (developing solvent: hexane:ethyl acetate=1:1) and recrystallized in hexane and ethyl acetate, to recover 6,7-dihydroxy-10,11-dihydrodibenz[b,f]oxepin-10-one (Compound 8) in colorless needle crystal (1.9 g; yield of 77%).

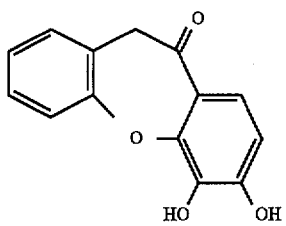

Formula (10)

The Compound 8 has a melting point of 180.7° to 182.4° C. By ¹H-NMR (90 MHz, DMSO-d₆), the Compound 8 has the peaks shown below.

δ(ppm) 4.04 (2H, s, Ar—CH₂) 6.69 (1H, d, J=8.8 Hz, Ar—H)
7.2–7.6 (5H, m, Ar—H)

[EXAMPLE 9]

Production of 7,8,9-trihydroxy-10,11-dihydrodibenz[b,f]oxepin-10-one (Compound 9)

The same procedures as in the steps 1 to 3 of Example 8 were carried out except for the use of 3,4,5-trimethoxyphenol in place of 2,3-dimethoxyphenol in the step 1 of Example 8, to recover 7,8,9-trihydroxy-10,11-dihydrodibenz[b,f]oxepin-10-one (Compound 9) represented by the following formula (11) in pale yellow needle crystal.

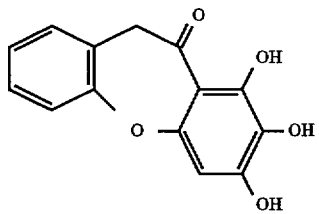

Formula (11)

The Compound 9 has a melting point of 166.5° to 168.5° C. By ¹H-NMR (90 MHz, CDCl₃), the Compound 9 has the peaks shown below.

δ(ppm) 4.08 (2H, s, Ar—CH₂) 5.31 (1H, brs, OH) 6.07 (1H, brs, OH) 6.53 (1H, s, Ar—H) 7.2–7.4 (4H, m, Ar—H) 13.05 (1H, s, OH)

[EXAMPLE 10]

Production of 6,7,8-trihydroxy-10,11-dihydrodibenz[b,f]oxepin-10-one (Compound 10)

2,3,4-Trimethoxybenzaldehyde (5 g) was suspended in anhydrous methylene chloride (50 ml), followed by addition of m-chloroperbenzoic acid (10 g; purity of 70%) to heat and stir the resulting mixture at 50° C. for 3 hours. After distilling off the solvents under reduced pressure, the residue was dissolved in ethyl acetate (100 ml) and washed in an aqueous saturated sodium hydrogen carbonate solution, in water and in a saturated sodium chloride solution, and dried over anhydrous magnesium sulfate. Then, the solvents were distilled off under reduced pressure. To the residue were added dioxane (15 ml) and a 3N sodium hydroxide solution (15 ml), prior to stirring at room temperature for 30 minutes and adjustment to acidity with dilute hydrochloric acid, followed by ethyl acetate extraction three times. The organic phase was washed in water and in a saturated sodium chloride solution and dried over anhydrous magnesium sulfate, followed by distillation of the solvents under reduced pressure. The residue was purified by silica gel column chromatography (developing solvent: hexane:ethyl acetate=3:1), to recover 2,3,4-trimethoxyphenol (2.4 g; yield of 51%). By ¹H-NMR (90 MHz, CDCl₃), the compound has the peaks shown below.

δ(ppm) 3.81 (3H, s, OCH₃) 3.89 (3H, s, OCH₃) 3.96 (3H, s, OCH₃) 6.54 (1H, d, J=8.5 Hz, Ar—H) 6.66 (1H, d, J=8.5 Hz, Ar—H)

The same procedures as in the steps 1 to 3 of Example 8 were carried out except for the use of the above compound in place of 2,3-dimethoxyphenol in the step 1 of Example 8, to recover 6,7,8-trihydroxy-10,11-dihydrodibenz[b,f]oxepin-10-one (Compound 10) represented by the following formula (12) in skin-colored irregular-shape crystal.

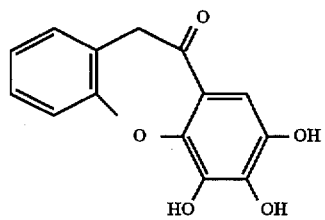

Formula (12)

The Compound 10 has a melting point of 193.3° to 195.3° C. By ¹H-NMR (90 MHz, DMSO-d₆), the Compound 10 has the peaks shown below.

δ(ppm) 3.99 (2H, s, CH₂) 6.85 (1H, s, Ar—H) 7.2–7.5 (4H, m, Ar—H)

[EXAMPLE 11]

Production of 7,9-dihydroxy-10,11-dihydrodibenz[b,f]oxepin-10-one (Compound 11)

The same procedures as in the steps 1 to 3 of Example 8 were carried out except for the use of 3,5-dimethoxyphenol in place of 2,3-dimethoxyphenol in the step 1 of Example 8, to recover 7,9-dihydroxy-10,11-dihydrodibenz[b,f]oxepin-10-one (Compound 11) represented by the following formula (13) in pale yellow needle crystal.

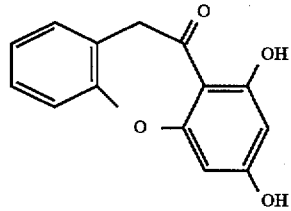

Formula (13)

The Compound 11 has a melting point of 191.5° to 193.5° C. By ¹H-NMR (90 MHz, DMSO-d₆), the Compound 11 has the peaks shown below.

δ(ppm) 4.13 (2H, s, Ar—CH₂) 6.14 (1H, d, J=2.4 Hz, Ar—H) 6.42 (1H, d, J=2.4 Hz, Ar—H) 7.2–7.6 (4H, m, Ar—H) 13.04 (1H, s, OH)

[EXAMPLE 12]

Production of 10,11-dihydrodibenz[b,f]oxepin-1,3-diol (Compound 12)

Step 1

The same procedures as in the steps 1 and 2 of Example 8 were carried out except for the use of 3,5-dimethoxyphenol in place of 2,3-dimethoxyphenol in the step 1 of Example 8, to recover 7,9-dimethoxy-10,11-dihydrodibenz[b,f]oxepin-10-one (0.72 g). Anhydrous methanol (5 ml) was added to the above compound, which was then stirred at 0° C. in argon stream. To the stirred mixture was added sodium boron hydride (0.2 g), followed by stirring at room temperature for one hour. The resulting solution was adjusted to acidity with dilute hydrochloric acid and extracted into ethyl acetate three times. The resulting organic phase was washed in water and in a saturated sodium chloride solution, and dried over anhydrous magnesium sulfate. Then, the solvents were distilled off under reduced pressure.

Step 2

The residue was placed in a pressure-resistant reaction vessel, followed by addition of pyridine hydrochloride salt (3 g) and stirring at 200° C. for 1.5 hours. Ethyl acetate and water were added to the resulting mixture for partition, and the resulting organic phase was washed in dilute hydrochloric acid and in water, and subsequently in a saturated sodium chloride solution, and dried over anhydrous magnesium sulfate. The solvents were distilled off under reduced pressure.

Step 3

The residue was dissolved in ethyl acetate, followed by addition of hydrogen through catalyst platinum dioxide, and the resulting product was purified by silica gel column chromatography (developing solvent: ethyl acetate:hexane= 1:2) and recrystallized in chloroform and hexane, to yield 10,11-dihydrodibenz[b,f]oxepin-1,3-diol (Compound 12) represented by the following formula (14) in skin-colored irregular-shape crystal (240 mg; yield of 40%).

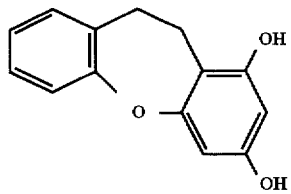

Formula (14)

The Compound 12 has a melting point of 145.3° to 147.2° C. By $^1$H-NMR (90 MHz, CDCl$_3$), the Compound 12 has the peaks shown below.

δ(ppm) 2.8–3.0 (2H, m, CH$_2$) 3.1–3.3 (2H, m, CH$_2$) 4.73 (1H, brs, OH) 4.81 (1H, brs, OH) 6.08 (1H, d, J=2.4 Hz, Ar—H) 6.31 (1H, d, J=2.4 Hz, Ar—H) 7.0–7.2 (4H, m, Ar—H)

[EXAMPLE 13]

Production of 7,8-dihydroxy-10,11-dihydrodibenz[b,f]oxepin-10-one (Compound 13)

The same procedures as in the steps 1 to 3 of Example 8 were carried out except for the use of 3,4-dimethoxyphenol in place of 2,3-dimethoxyphenol in the step 1 of Example 8, to recover 7,8-dihydroxy-10,11-dihydrodibenz[b,f]oxepin-10-one (Compound 13) represented by the following formula (15) in pale yellow plate crystal.

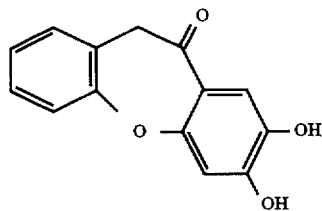

Formula (15)

The Compound 13 has a melting point of 198.1° to 200.4° C. By $^1$H-NMR (90 MHz, DMSO-d$_6$), the Compound 13 has the peaks shown below.

δ(ppm) 3.99 (2H, s, Ar—CH$_2$) 6.78 (1H, s, Ar—H) 7.1–7.4 (5H, m, Ar—H)

[EXAMPLE 14]

Production of 10,11-dihydrodibenz[b,f]oxepin-2,3-diol (Compound 14)

The same procedures as in the steps 1 to 3 of Example 12 were carried out except for the use of 7,8-dimethoxy-10,11-dihydrodibenz[b,f]oxepin-10-one produced in the step 2 of Example 13 as a starting material in the process of Example 12, to recover 10,11-dihydrodibenz[b,f]oxepin-2,3-diol (Compound 14) represented by the following formula (16) in colorless plate crystal.

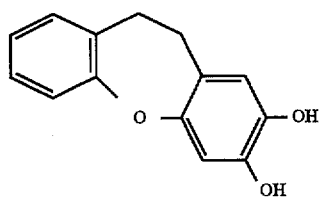

Formula (16)

The Compound 14 has a melting point of 150.6° to 152.6° C. By $^1$H-NMR (90 MHz, CDCl$_3$), the Compound 14 has the peaks shown below.

δ(ppm) 2.9–3.2 (2H, m, CH$_2$) 2.9–3.2 (2H, m, CH$_2$) 4.8–5.2 (1H, brs, OH) 6.61 (1H, s, Ar—H) 6.73 (1H, s, Ar—H) 6.9–7.2 (4H, m, Ar—H)

[EXAMPLE 15]

Production of 3-chloro-7,9-dihydroxy-10,11-dihydrodibenz[b,f]oxepin-10-one (Compound 15)

The same procedures as in the steps 1 to 3 of Example 8 were carried out except for the use of 3,5-dimethoxyphenol and 2',4'-dichloroacetophenone in place of 2,3-dimethoxyphenol and 2'-bromoacetophenone, respectively, in the step 1 of Example 8, to recover 3-chloro-7,9-dihydroxy-10,11-dihydrodibenz[b,f]oxepin-10-one (Compound 15) represented by the following formula (17) in colorless needle crystal.

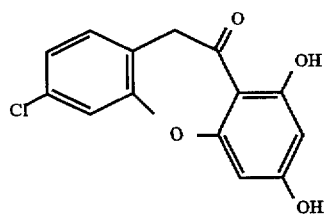

Formula (17)

The Compound 15 has a melting point of 236.5° to 238.5° C. By $^1$H-NMR (90 MHz, DMSO-d$_6$), the Compound 15 has the peaks shown below.

δ(ppm) 4.12 (2H, s, Ar—CH$_2$) 6.11 (1H, d, J=2.4 Hz, Ar—H) 6.40 (1H, d, J=2.4 Hz, Ar—H) 7.3–7.5 (3H, m, Ar—H) 12.98 (1H, s, OH)

[EXAMPLE 16]

Production of 7-chloro-10,11-dihydrodibenz[b,f]oxepin-1,3-diol (Compound 16)

The same procedures as in Example 12 were carried out except for the use of 3-chloro-7,9-dimethoxy-10,11-dihydrodibenz[b,f]oxepin-10-one produced in the step 2 of Example 15 as a starting material in the process of Example 12, to recover 7-chloro-10,11-dihydrodibenz[b,f]oxepin-1,3-diol (Compound 16) represented by the following formula (18) in skin-colored plate crystal.

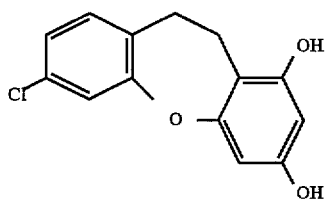

Formula (18)

The Compound 16 has a melting point of 185.5° to 187.5° C. By ¹H-NMR (90 MHz, DMSO-d₆), the Compound 16 has the peaks shown below.

δ(ppm) 2.6–2.8 (2H, m, CH₂) 2.8–3.1 (2H, m, CH₂) 6.0–6.2 (2H, m, Ar—H) 7.1–7.3 (3H, m, Ar—H) 9.3 (1H, br, OH) 9.4 (1H, br, OH)

[EXAMPLE 17]

Production of 3-chloro-7,8-dihydroxy-10,11-dihydrodibenz[b,f]oxepin-10-one (Compound 17)

The same procedures as in the steps 1 to 3 of Example 8 were carried out except for the use of 3,4-dimethoxyphenol and 2',4'-dichloroacetophenone in place of 2,3-dimethoxyphenol and 2'-bromoacetophenone, respectively, in the step 1 of Example 8, to recover 3-chloro-7,8-dihydroxy-10,11-dihydrodibenz[b,f]oxepin-10-one (Compound 17) represented by the following formula (19) in mud yellow needle crystal.

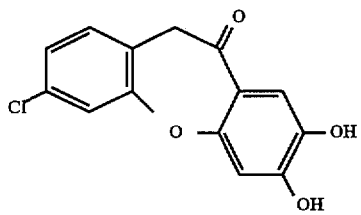

Formula (19)

The Compound 17 has a melting point of 248.1° to 250.1° C. By ¹H-NMR (90 MHz, DMSO-d₆), the Compound 17 has the peaks shown below.

δ(ppm) 4.00 (2H, s, Ar—CH₂) 6.80 (1H, s, Ar—H) 7.32 (1H, s, Ar—H) 7.3–7.5 (3H, m, Ar—H)

[EXAMPLE 18]

Production of 7-chloro-10,11-dihydrodibenz[b,f]oxepin-2,3-diol (Compound 18)

The same procedures as in Example 12 were carried out except for the use of 3-chloro-7,8-dimethoxy-10,11-dihydrodibenz[b,f]oxepin-10-one produced in the step 2 of Example 17 as a starting material in the process of Example 12, to recover 7-chloro-10,11-dihydrodibenz[b,f]oxepin-2,3-diol (Compound 18) represented by the following formula (20) in colorless needle crystal.

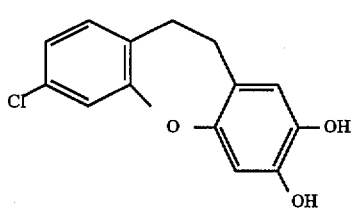

Formula (20)

The Compound 18 has a melting point of 119.9° to 121.9° C. By ¹H-NMR (90 MHz, CDCl₃), the Compound 18 has the peaks shown below.

δ(ppm) 2.9–3.1 (2H, m, CH₂) 2.9–3.1 (2H, m, CH₂) 5.01 (1H, brs, OH) 6.62 (1H, s, Ar—H) 6.71 (1H, s, Ar—H) 7.0–7.2 (3H, m, Ar—H)

[EXAMPLE 19]

Production of 2-chloro-7,9-dihydroxy-10,11-dihydrodibenz[b,f]oxepin-10-one (Compound 19)

The same procedures as in the steps 1 to 3 of Example 8 were carried out except for the use of 3,5-dimethoxyphenol and 2',5'-dichloroacetophenone in place of 2,3-dimethoxyphenol and 2'-bromoacetophenone, respectively, in the step 1 of Example 8, to recover 2-chloro-7,9-dihydroxy-10,11-dihydrodibenz[b,f]oxepin-10-one (Compound 19) represented by the following formula (21) in colorless needle crystal.

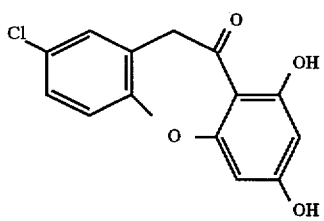

Formula (21)

The Compound 19 has a melting point of 183.1° to 184.2° C. By ¹H-NMR (90 MHz, DMSO-d₆), the Compound 19 has the peaks shown below.

δ(ppm) 4.14 (2H, s, Ar—CH₂) 6.11 (1H, d, J=2.4 Hz, Ar—H) 6.39 (1H, d, J=2.4 Hz, Ar—H) 7.3–7.4 (2H, m, Ar—H) 7.5–7.6 (1H, m, Ar—H) 12.97 (1H, s, OH)

[EXAMPLE 20]

Production of 8-chloro-10,11-dihydrodibenz[b,f]oxepin-1,3-diol (Compound 20)

The same procedures as in Example 12 were carried out except for the use of 2-chloro-7,9-dimethoxy-10,11-dihydrodibenz[b,f]oxepin-10-one produced in the step 2 of Example 19 as a starting material in the process of Example 12, to recover 8-chloro-10,11-dihydrodibenz[b,f]oxepin-1,3-diol (Compound 20) represented by the following formula (22) in pale orange needle crystal.

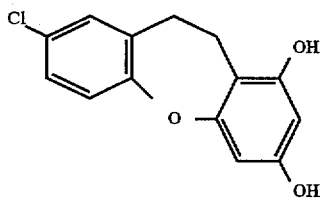

Formula (22)

The Compound 20 has a melting point of 166.2° to 168.2° C. By ¹H-NMR (90 MHz, DMSO-d₆), the Compound 20 has the peaks shown below.

δ(ppm) 2.7–2.9 (2H, m, CH$_2$) 2.9–3.1 (2H, m, CH$_2$) 6.0–6.2 (2H, m, Ar—H) 7.1–7.3 (3H, m, Ar—H) 9.2 (1H, br, OH) 9.4 (1H, br, OH)

[EXAMPLE 21]

Production of 2-chloro-7,8-dihydroxy-10,11-dihydrodibenz[b,f]oxepin-10-one (Compound 21)

The same procedures as in the steps 1 to 3 of Example 8 were carried out except for the use of 3,4-dimethoxyphenol and 2',5'-dichloroacetophenone in place of 2,3-dimethoxyphenol and 2'-bromoacetophenone, respectively, in the step 1 of Example 8, to recover 2-chloro-7,8-dihydroxy-10,11-dihydrodibenz[b,f]oxepin-10-one (Compound 21) represented by the following formula (23) in orange needle crystal.

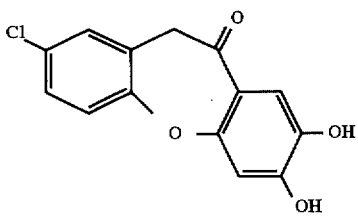

Formula (23)

The Compound 21 has a melting point of 236.0° to 238.0° C. By $^1$H-NMR (90 MHz, DMSO-d$_6$), the Compound 21 has the peaks shown below.

δ(ppm) 4.00 (2H, s, Ar—CH$_2$) 6.77 (1H, s, Ar—H) 7.26 (1H, s, Ar—H) 7.3–7.6 (3H, m, Ar—H)

[EXAMPLE 22]

Production of 8-chloro-10,11-dihydrodibenz[b,f]oxepin-2,3-diol (Compound 22)

The same procedures as in Example 12 were carried out except for the use of 2-chloro-7,8-dimethoxy-10,11-dihydrodibenz[b,f]oxepin-10-one produced in the step 2 of Example 21 as a starting material in the process of Example 12, to recover 8-chloro-10,11-dihydrodibenz[b,f]oxepin-2,3-diol (Compound 22) represented by the following formula (24) in yellow plate crystal.

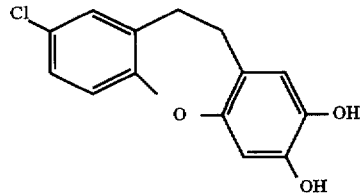

Formula (24)

The Compound 22 has a melting point of 168.2° to 170.2° C. By $^1$H-NMR (90 MHz, DMSO-d$_6$), the Compound 22 has the peaks shown below.

δ(ppm) 2.7–3.1 (2H, m, CH$_2$) 2.7–3.1 (2H, m, CH$_2$) 6.51 (1H, s, Ar—H) 6.55 (1H, s, Ar—H) 7.0–7.4 (3H, m, Ar—H) 8.8 (1H, brs, OH) 8.8 (1H, brs, OH)

[EXAMPLE 23]

Production of 3-fluoro-7,9-dihydroxy-10,11-dihydrodibenz[b,f]oxepin-10-one (Compound 23)

The same procedures as in the steps 1 to 3 of Example 8 were carried out except for the use of 3,5-dimethoxyphenol and 2',4'-difluoroacetophenone in place of 2,3-dimethoxyphenol and 2'-bromoacetophenone, respectively, in the step 1 of Example 8, to recover 3-fluoro-7,9-dihydroxy-10,11-dihydrodibenz[b,f]oxepin-10-one (Compound 23) represented by the following formula (25) in mud yellow plate crystal.

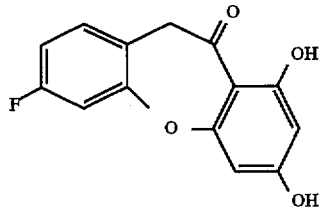

Formula (25)

The Compound 23 has a melting point of 178.5° to 180.5° C. By $^1$H-NMR (90 MHz, DMSO-d$_6$), the Compound 23 has the peaks shown below.

δ(ppm) 4.10 (2H, s, Ar—CH$_2$) 6.10 (1H, d, J=2.3 Hz, Ar—H) 6.38 (1H, d, J=2.3 Hz, Ar—H) 7.0–7.6 (3H, m, Ar—H) 12.99 (1H, s, OH)

[EXAMPLE 24]

Production of 7-fluoro-10,11-dihydrodibenz[b,f]oxepin-1,3-diol (Compound 24)

The same procedures as in Example 12 were carried out except for the use of 7,9-dimethoxy-3-fluoro-10,11-dihydrodibenz[b,f]oxepin-10-one produced in the step 2 of Example 23 as a starting material in the process of Example 12, to recover 7-fluoro-10,11-dihydrodibenz[b,f]oxepin-1,3-diol (Compound 24) represented by the following formula (26) in colorless needle crystal.

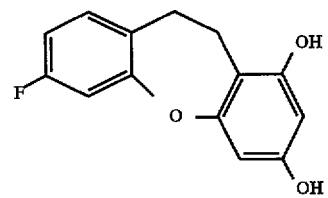

Formula (26)

The Compound 24 has a melting point of 177.7° to 179.7° C. By $^1$H-NMR (90 MHz, DMSO-d$_6$), the Compound 24 has the peaks shown below.

δ(ppm) 2.5–2.8 (2H, m, CH$_2$) 2.9–3.1 (2H, m, CH$_2$) 6.07 (1H, d, J=2.3 Hz, Ar—H) 6.12 (1H, d, J=2.3 Hz, Ar—H) 6.8–7.4 (3H, m, Ar—H) 9.2–9.5 (1H, br, OH)

[EXAMPLE 25]

Production of 3-fluoro-7,8-dihydroxy-10,11-dihydrodibenz[b,f]oxepin-10-one (Compound 25)

The same procedures as in the steps 1 to 3 of Example 8 were carried out except for the use of 3,4-dimethoxyphenol and 2',4'-difluoroacetophenone in place of 2,3-dimethoxyphenol and 2'-bromoacetophenone, respectively, in the step 1 of Example 8, to recover 3-fluoro-7,8-dihydroxy-10,11-dihydrodibenz[b,f]oxepin-10-one (Compound 25) represented by the following formula (27) in colorless needle crystal.

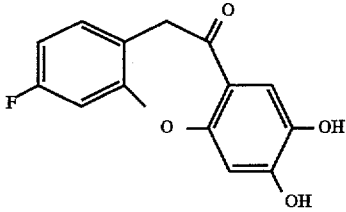

Formula (27)

The Compound 25 has a melting point of 195.1° to 197.1° C. By ¹H-NMR (90 MHz, DMS-d₆), the Compound 25 has the peaks shown below.

δ(ppm) 3.99 (2H, s, Ar—CH₂) 6.80 (1H, s, Ar—H) 6.9–7.5 (3H, m, Ar—H) 7.28 (1H, s, Ar—H)

[EXAMPLE 26]

Production of 7-fluoro-10,11-dihydrodibenz[b,f] oxepin-2,3-diol (Compound 26)

The same procedures as in Example 12 were carried out except for the use of 7,8-dimethoxy-3-fluoro-10,11-dihydrodibenz[b,f]oxepin-10-one produced in the step 2 of Example 25 as a starting material in the process of Example 12, to recover 7-fluoro-10,11-dihydrodibenz[b,f]oxepin-2,3-diol (Compound 26) represented by the following formula (28) in pale mud yellow plate crystal.

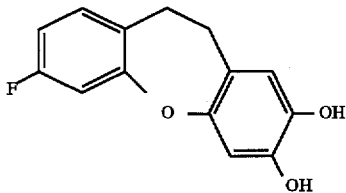

Formula (28)

The Compound 26 has a melting point of 105.8° to 107.4° C. By ¹H-NMR (90 MHz, CDCl₃), the Compound 26 has the peaks shown below.

δ(ppm) 2.9–3.1 (2H, m, CH₂) 2.9–3.1 (2H, m, CH₂) 6.62 (1H, s, Ar—H) 6.71 (1H, s, Ar—H) 6.7–7.1 (3H, m, Ar—H)

[EXAMPLE 27]

Production of 3,4-dichloro-7,9-dihydroxy-10,11-dihydrodibenz[b, f]oxepin-10-one (Compound 27)

The same procedures as in the steps 1 to 3 of Example 8 were carried out except for the use of 3,5-dimethoxyphenol and 2',3', 4'-trichloroacetophenone in place of 2,3-dimethoxyphenol and 2'-bromoacetophenone, respectively, in the step 1 of Example 8, to recover 3,4-dichloro-7,9-dihydroxy-10,11-dihydrodibenz[b,f]oxepin-10-one (Compound 27) represented by the following formula (29) in yellow plate crystal.

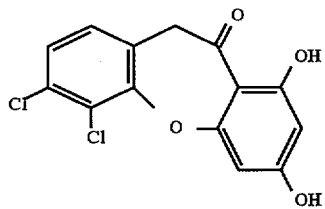

Formula (29)

The Compound 27 has a melting point of 222.2° to 224.2° C. By ¹H-NMR (90 MHz, DMSO-d₆), the Compound 27 has the peaks shown below.

δ(ppm) 4.20 (2H, s, Ar—CH₂) 6.13 (1H, d, J=2.4 Hz, Ar—H) 6.48 (1H, d, J=2.4 Hz, Ar—H) 7.4–7.5 (2H, m, Ar—H) 12.90 (1H, s, OH)

[EXAMPLE 28]

Production of 6,7-dichloro-10,11-dihydrodibenz[b,f] oxepin-1,3-diol (Compound 28)

The same procedures as in Example 12 were carried out except for the use of 3,4-dichloro-7,9-dimethoxy-10,11-dihydrodibenz[b,f]oxepin-10-one produced in the step 2 of Example 27 as a starting material in the process of Example 12, to recover 6,7-dichloro-10,11-dihydrodibenz[b,f]oxepin-1,3-diol (Compound 28) represented by the following formula (30) in colorless needle crystal.

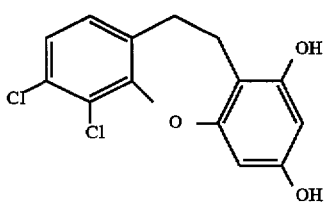

Formula (30)

The Compound 28 has a melting point of 172.2° to 174.0° C. By ¹H-NMR (90 MHz, DMSO-d₆), the Compound 28 has the peaks shown below.

δ(ppm) 2.6–2.8 (2H, m, CH₂) 3.0–3.2 (2H, m, CH₂) 6.14 (1H, d, J=2.5 Hz, Ar—H) 6.21 (1H, d, J=2.5 Hz, Ar—H) 7.25 (1H, d, J=8.3 Hz, Ar—H) 7.38 (1H, d, J=8.3 Hz, Ar—H) 9.3–9.6 (1H, br, OH) 9.3–9.6 (1H, br, OH)

[EXAMPLE 29]

Production of 2-fluoro-7,9-dihydroxy-10,11-dihydrodibenz[b,f]oxepin-10-one (Compound 29)

A solution (100 ml) of 2,5-difluorobenzaldehyde (24.6 g) in tetrahydrofuran was dropwise added to an ice-cooled solution (207 ml) of 0.92N magnesium methylbromide in tetrahydrofuran. The resulting solution was stirred at room temperature for 1.5 hours, and the organic phase was washed in a saturated sodium chloride solution and dried over anhydrous magnesium sulfate, to subsequently distill off the solvents under reduced pressure. To the residue were added anhydrous dichloromethane (500 ml), sodium acetate (14.2 g) and pyridinium chlorochromate (55.94 g), prior to stirring at room temperature for 10 hours. To the resulting mixture was added an aqueous saturated sodium hydrogen carbonate solution, prior to extraction in ethyl acetate three times. The organic phase was washed in water and in a saturated sodium chloride solution and dried over anhydrous magnesium sulfate, to distill off the solvents under reduced pressure. The residue was purified by silica gel column chromatography (developing solvent: hexane:ethyl acetate= 85:15), to recover 2',5'-difluoroacetophenone (22.73 g; yield of 84%). By ¹H-NMR (90 MHz, CDCl₃), the compound has the peaks shown below.

δ(ppm) 2.63 (3H, d, ⁵$J_{HF}$=5 Hz, CH₃) 7.1–7.2 (2H, m, Ar—H) 7.4–7.5 (1H, m, Ar—H)

The same procedures as in the steps 1 to 3 of Example 8 were carried out except for the use of the compound in place of 2'-bromoacetophenone and the use of 3,5-dimethoxyphenol in place of 2,3-dimethoxyphenol in the step 1 of Example 8, to recover 2-fluoro-7,9-dihydroxy-10, 11-dihydrodibenz[b,f]oxepin-10-one (Compound 29) represented by the following formula (31) in pale yellow needle crystal.

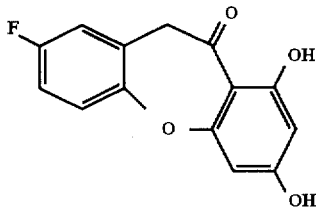

Formula (31)

The Compound 29 has a melting point of 162.9° to 164.0° C. By ¹H-NMR (90 MHz, DMSO-d₆), the Compound 29 has the peaks shown below.

δ(ppm) 4.10 (2H, s, Ar—CH₂) 6.08 (1H, d, J=2 Hz, Ar—H) 6.35 (1H, d, J=2 Hz, Ar—H) 7.1–7.4 (3H, m, Ar—H) 11.1 (1H, br, OH) 12.94 (1H, s, OH)

[EXAMPLE 30]

Production of 8-fluoro-10,11-dihydrodibenz[b,f]oxepin-1,3-diol (Compound 30)

The same procedures as in Example 12 were carried out except for the use of 2-fluoro-7,9-dimethoxy-10,11-dihydrodibenz[b,f]oxepin-10-one produced in the step 2 of Example 29 as a starting material in the process of Example 12, to recover 8-fluoro-10,11-dihydrodibenz[b,f]oxepin-1,3-diol (Compound 30) represented by the following formula (32) in colorless irregular-shape crystal.

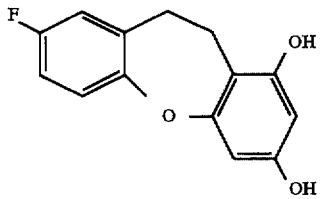

Formula (32)

The Compound 30 has a melting point of 148.2° to 150.5° C. By ¹H-NMR (90 MHz, CDCl₃), the Compound 30 has peaks shown below.

δ(ppm) 2.7–2.8 (2H, m, CH₂) 2.9–3.0 (2H, m, CH₂) 6.0–6.1 (2H, m, Ar—H) 7.0–7.1 (3H, m, Ar—H) 9.17 (1H, s, OH) 9.37 (1H, s, OH)

[EXAMPLE 31]

Production of 2-fluoro-7,8-dihydroxy-10,11-dihydrodibenz[b,f]oxepin-10-one (Compound 31)

The same procedures as in the steps 1 to 3 of Example 29 were carried out except for the use of 3,4-dimethoxyphenol in place of 3,5-dimethoxyphenol in the process of Example 29, to recover 2-fluoro-7,8-dihydroxy-10,11-dihydrodibenz[b,f]oxepin-10-one (Compound 31) represented by the following formula (33) in colorless needle crystal.

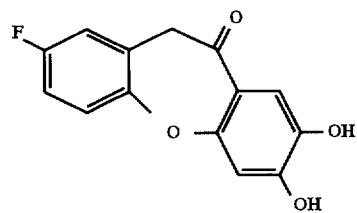

Formula (33)

The Compound 31 has a melting point of 226.5° to 228.5° C. By ¹H-NMR (90 MHz, DMSO-d₆), the Compound 31 has the peaks shown below.

δ(ppm) 3.99 (2H, s, Ar—CH₂) 6.77 (1H, s, Ar—H) 6.9–7.0 (4H, m, Ar—H) 9.74 (1H, br, OH) 9.74 (1H, br, OH)

[EXAMPLE 32]

Production of 8-fluorodibenz[b,f]oxepin-2,3-diol (Compound 32)

The same procedures as in the steps 1 and 2 of Example 12 were carried out except for the use of 2-fluoro-7,8-dimethoxy-10,11-dihydrodibenz[b,f]oxepin-10-one produced in the step 2 of Example 31 as a starting material in the process of Example 12, to recover 8-fluorodibenz[b,f]oxepin-2,3-diol (Compound 32) represented by the following formula (34) in colorless plate crystal.

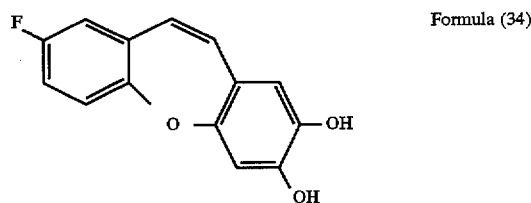

Formula (34)

The Compound 32 has a melting point of 207.0° to 209.0° C. By ¹H-NMR (90 MHz, DMSO-d₆), the Compound 32 has peaks shown below.

δ(ppm) 6.49 (1H, d, J=11 Hz, CH) 6.61 (1H, d, J=11 Hz, CH) 6.66 (1H, s, Ar—H) 6.66 (1H, s, Ar—H) 7.0–7.2 (3H, m, Ar—H) 9.16 (1H, br, OH) 9.16 (1H, br, OH)

[EXAMPLE 33]

Production of 8-fluoro-10,11-dihydrodibenz[b,f]oxepin-2,3-diol (Compound 33)

The same procedures as in the steps 1 to 3 of Example 12 were carried out except for the use of 2-fluoro-7,8-dimethoxy-10,11-dihydrodibenz[b,f]oxepin-10-one produced in the step 2 of Example 31 as a starting material in the process of Example 12, to recover 8-fluoro-10,11-dihydrodibenz[b,f]oxepin-2,3-diol (Compound 33) represented by the following formula (35) in colorless plate crystal.

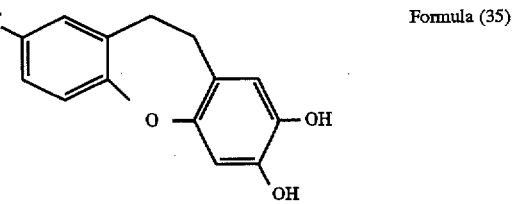

Formula (35)

The Compound 33 has a melting point of 148.0° to 151.0° C. By ¹H-NMR (90 MHz, DMSO-d₆), the Compound 33 has peaks shown below.

δ(ppm) 2.9–3.0 (2H, m, CH₂) 2.9–3.0 (2H, m, CH₂) 6.50 (1H, s, Ar—H) 6.55 (1H, s, Ar—H) 6.8–7.2 (3H, m, Ar—H) 8.64 (1H, s, OH) 8.90 (1H, s, OH)

[EXAMPLE 34]

Production of 2,4-dichloro-7,9-dihydroxy-10,11-dihydrodibenz[b,f]oxepin-10-one (Compound 34)

The same procedures as in Example 29 were carried out except for the use of 2,3,5-trichlorobenzaldehyde in place of 2,5-difluorobenzaldehyde in the process of Example 29, to recover 2,4-dichloro-7,9-dihydroxy-10,11-dihydrodibenz[b,f]oxepin-10-one (Compound 34) represented by the following formula (36) in pale red needle crystal.

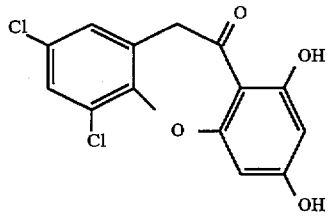

Formula (36)

The Compound 34 has a melting point of 224.0° to 225.7° C. By ¹H-NMR (90 MHz, DMSO-d₆), the Compound 34 has the peaks shown below.

δ(ppm) 4.20 (2H, s, Ar—CH₂) 6.14 (1H, d, J=2.2 Hz, Ar—H) 6.44 (1H, d, J=2.2 Hz, Ar—H) 7.60 (1H, d, J=2.4 Hz, Ar—H) 7.67 (1H, d, J=2.4 Hz, Ar—H)

[EXAMPLE 35]

Production of 6,8-dichloro-10,11-dihydrodibenz[b,f]oxepin-1,3-diol (Compound 35)

The same procedures as in Example 12 were carried out except for the use of 2,4-dichloro-7,9-dimethoxy-10,11-dihydrodibenz[b,f]oxepin-10-one produced in the step 2 of Example 34 as a starting material in the process of Example 12, to recover 6,8-dichloro-10,11-dihydrodibenz[b,f]oxepin-1,3-diol (Compound 35) represented by the following formula (37) in colorless needle crystal.

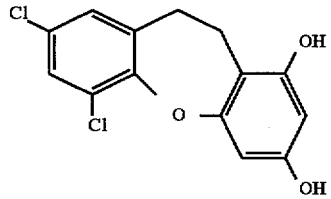

Formula (37)

The Compound 35 has a melting point of 160.5° to 161.5° C. By ¹H-NMR (90 MHz, DMSO-d₆), the Compound 35 has peaks shown below.

δ(ppm) 2.6–2.8 (2H, m, CH₂) 3.0–3.2 (2H, m, CH₂) 6.13 (1H, d, J=2.5 Hz, Ar—H) 6.18 (1H, d, J=2.5 Hz, Ar—H) 7.36 (1H, d, J=2.7 Hz, Ar—H) 7.49 (1H, d, J=2.7 Hz, Ar—H)

[EXAMPLE 36]

Production of 4-chloro-7,9-dihydroxy-10,11-dihydrodibenz[b,f]oxepin-10-one (Compound 36)

The same procedures as in Example 29 were carried out except for the use of 2,3-dichlorobenzaldehyde in place of 2,5-difluorobenzaldehyde in the process of Example 29, to recover 4-chloro-7,9-dihydroxy-10,11-dihydrodibenz[b,f]oxepin-10-one (Compound 36) represented by the following formula (38) in colorless needle crystal.

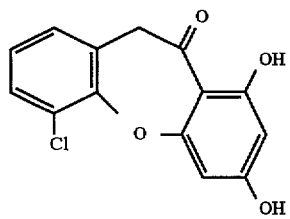

Formula (38)

The Compound 36 has a melting point of 163.0° to 163.8° C. By ¹H-NMR (90 MHz, DMSO-d₆), the Compound 36 has the peaks shown below.

δ(ppm) 4.18 (2H, s, Ar—CH₂) 6.13 (1H, d, J=2.4 Hz, Ar—H) 6.47 (1H, d, J=2.4 Hz, Ar—H) 7.1–7.5 (3H, m, Ar—H) 12.93 (1H, s, OH)

[EXAMPLE 37]

Production of 6-chloro-10,11-dihydrodibenz[b,f]oxepin-1,3-diol (Compound 37)

The same procedures as in Example 12 were carried out except for the use of 4-chloro-7,9-dimethoxy-10,11-dihydrodibenz[b,f]oxepin-10-one produced in the step 2 of Example 36 as a starting material in the process of Example 12, to recover 6-chloro-10,11-dihydrodibenz[b,f]oxepin-1,3-diol (Compound 37) represented by the following formula (39) in pale yellow plate crystal.

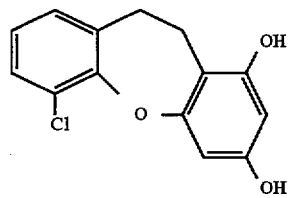

Formula (39)

The Compound 37 has a melting point of 202.5° to 203.0° C. By ¹H-NMR (90 MHz, DMSO-d₆), the Compound 37 has the peaks shown below.

δ(ppm) 2.6–2.9 (2H, m, CH₂) 2.9–3.2 (2H, m, CH₂) 6.12 (1H, d, J=2.4 Hz, Ar—H) 6.20 (1H, d, J=2.4 H z, Ar—H) 7.0–7.4 (3H, m, Ar—H)

[EXAMPLE 38]

Production of 7,9-dihydroxy-2-trifluoromethyl-10,11-dihydrodibenz[b,f]oxepin-10-one (Compound 38)

The same procedures as in Example 29 were carried out except for the use of 2-chloro-5-trifluoromethylbenzaldehyde in place of 2,5-difluorobenzaldehyde in the process of Example 29, to recover 7,9-dihydroxy-2-trifluoromethyl-10,11-dihydrodibenz[b,f]oxepin-10-one (Compound 38) represented by the following formula (40) in pale mud yellow needle crystal.

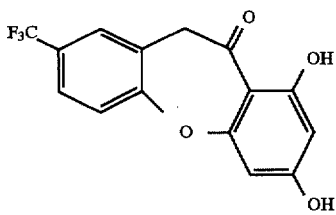

Formula (40)

The Compound 38 has a melting point of 172.9° to 174.7° C. By ¹H-NMR (90 MHz, DMSO-d₆), the Compound 38 has the peaks shown below.

δ(ppm) 4.25 (2H, s, Ar—CH₂) 6.11 (1H, d, J=2.5 Hz, Ar—H) 6.42 (1H, d, J=2.5 Hz, Ar—H) 7.5–7.9 (3H, m, Ar—H) 12.96 (1H, s, OH)

[EXAMPLE 39]

Production of 8-trifluoromethyl-10,11-dihydrodibenz[b,f]oxepin-1,3-diol (Compound 39)

The same procedures as in Example 12 were carried out except for the use of 7,9-dimethoxy-2-trifluoromethyl-10,11-dihydrodibenz[b,f]oxepin-10-one produced in the step 2 of Example 38 as a starting material in the process of Example 12, to recover 8-trifluoromethyl-10,11-dihydrodibenz[b,f]oxepin-1,3-diol (Compound 39) represented by the following formula (41) in pale pink plate crystal.

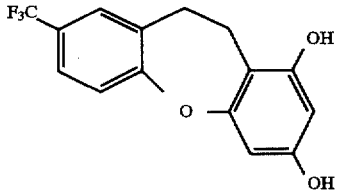

Formula (41)

The Compound 39 has a melting point of 177.9° to 179.9° C. By ¹H-NMR (90 MHz, CDCl₃), the Compound 39 has the peaks shown below.

δ(ppm) 2.9–3.0 (2H, m, CH₂) 3.1–3.3 (2H, m, CH₂) 4.6–5.0 (1H, br, OH) 6.11 (1H, d, J=2.7 Hz, Ar—H) 6.32 (1H, d, J=2.7 Hz, Ar—H) 7.1–7.2 (1H, m, Ar—H) 7.4–7.6 (2H, m, Ar—H)

[EXAMPLE 40]

Production of 2,3,7,9-tetrahydroxy-10,11-dihydrodibenz[b,f]oxepin-10-one (Compound 40)

The same procedures as in Example 29 were carried out except for the use of 2-bromo-4,5-dimethoxybenzaldehyde in place of 2,5-difluorobenzaldehyde in the process of Example 29, to recover 2,3,7,9-tetrahydroxy-10,11-dihydrodibenz[b,f]oxepin-10-one (Compound 40) represented by the following formula (42) in brown irregular-shape crystal.

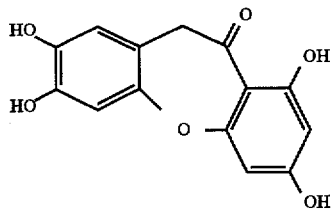

Formula (42)

By ¹H-NMR (90 MHz, DMSO-d₆), the Compound 40 has the peaks shown below.

δ(ppm) 3.85 (2H, s, Ar—CH₂) 6.04 (1H, d, J=2.3 Hz, Ar—H) 6.27 (1H, d, J=2.3 Hz, Ar—H) 6.68 (1H, s, Ar—H) 6.68 (1H, s, Ar—H) 9.0–9.3 (1H, br, OH) 12.93 (1H, s, OH)

[EXAMPLE 41]

Production of 4-propyl-10,11-dihydrodibenz[b,f]oxepin-1,3-diol (Compound 41)

Triphenylphosphine ethylbromide (4.1 g) was added to a 2N sodium hydride/dimethyl sulfoxide solution (11 ml), prior to agitation at 50° C. for 30 minutes. To the mixture was added 4,6-dimethoxy-2-hydroxybenzaldehyde (1 g), for agitation at 50° C. overnight. After the termination of the reaction, the resulting solution was partitioned with ethyl acetate and dilute hydrochloric acid, and the resulting ethyl acetate phase was washed in water and subsequently in a saturated sodium chloride solution and dried over anhydrous magnesium sulfate, to distill off the solvents under reduced pressure. The residue was purified by silica gel column chromatography (developing solvent: hexane:ethyl acetate= 3:1), followed by addition of a catalytic amount of platinum dioxide for hydrogenation, to recover 3,5-dimethoxy-2-propylphenol (0.5 g; yield of 46%). By ¹H-NMR (90 MHz, CDCl₃), the compound has the peaks shown below.

δ(ppm) 0.94 (3H, t, J=7.2 Hz, CH₃) 1.5–1.8 (2H, m, CH₂) 2.52(2H, t, J=7.5 Hz, Ar—CH₂) 3.76 (3H, s, OCH₃) 3.77 (3H, s, OCH₃) 6.04 (1H, d, J=2.4 Hz, Ar—H) 6.08 (1H, d, J=2.4 Hz, Ar—H)

The same procedures as in Example 12 were carried out except for the use of the above compound in place of 3,5-dimethoxyphenol in the step 1 of Example 12, to recover 4-propyl-10,11-dihydrodibenz[b,f]oxepin-1,3-diol (Compound 41) represented by the following formula (43) in red oil.

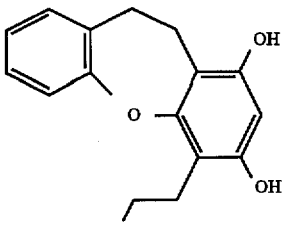

Formula (43)

By ¹H-NMR (90 MHz, CDCl₃), the Compound 41 has the peaks shown below.

δ(ppm) 1.03 (3H, t, J=7.2 Hz, CH₃) 1.4–1.8 (2H, m, CH₂) 2.6–2.8 (2H, m, CH₂) 2.9–3.2 (2H, m, CH₂) 2.9–3.2 (2H, m, CH₂) 4.71 (1H, brs, OH) 6.10 (1H, s, Ar—H) 6.9–7.2 (4H, m, Ar—H)

[EXAMPLE 42]

Production of 2-propyl-10,11-dihydrodibenz[b,f]oxepin-1,3-diol (Compound 42)

Anhydrous tetrahydrofuran (36 ml) was added to triphenylphosphine ethyl bromide (12.3 g) prior to stirring at room temperature for 20 minutes. To the resulting mixture was added potassium tert-butoxide (4.5 g), for stirring at room temperature for 30 minutes. Then, 2,6-dimethoxy-4-hydroxybenzaldehyde (3.0 g) was added to the resulting mixture for stirring at room temperature for 2 hours. After the termination of the reaction, the resulting solution was partitioned with ethyl acetate and dilute hydrochloric acid, and the resulting ethyl acetate phase was washed in water and subsequently in a saturated sodium chloride solution and dried over anhydrous magnesium sulfate, to distill off the solvents under reduced pressure. The residue was purified by silica gel column chromatography (developing solvent: hexane:ethyl acetate=2:1), followed by addition of a catalytic amount of platinum dioxide for hydrogenation, to recover 3,5-dimethoxy-4-propylphenol (1.8 g; yield of 55%). By $^1$H-NMR (90 MHz, CDCl$_3$), the compound has the peaks shown below.

δ(ppm) 0.89 (3H, t, J=7.2 Hz, CH$_3$) 1.3–1.6 (2H, m, CH$_2$) 2.51 (2H, t, J=7.5 Hz, Ar—CH$_2$) 3.75 (3H, s, OCH$_3$) 3.75 (3H, s, OCH$_3$) 4.71 (1H, s, OH) 6.05 (1H, s, Ar—H) 6.05 (1H, s, Ar—H)

The same procedures as in Example 12 were carried out except for the use of the above compound in place of 3,5-dimethoxyphenol in the step 1 of Example 12, to recover 2-propyl-10,11-dihydrodibenz[b,f]oxepin-1,3-diol (Compound 42) represented by the following formula (44) in yellow needle crystal.

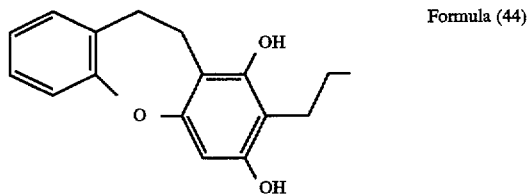

Formula (44)

The Compound 42 has a melting point of 109.4° to 111.4° C. By $^1$H-NMR (90 MHz, CDCl$_3$), the Compound 42 has the peaks shown below.

δ(ppm) 0.96 (3H, t, J=7.2 Hz, CH$_3$) 1.3–1.7 (2H, m, CH$_2$) 2.53 (2H, t, J=7.6 Hz, CH$_2$) 2.8–3.3 (2H, m, CH$_2$) 2.8–3.3 (2H, m, CH$_2$) 4.61 (1H, brs, OH) 4.74 (1H, brs, OH) 6.32 (1H, s, Ar—H) 7.0–7.2 (4H, m, Ar—H)

[EXAMPLE 43]

Production of 7,8-dihydroxy-10,11-dihydrodibenz[b,f]thiepin-10-one (Compound 43)

1,2-Dimethoxybenzene (10 g) was dissolved in methylene chloride (50 ml), prior to stirring at 0° C. To the resulting solution was added dropwise chlorosulfonic acid (23.5 ml), for stirring at 45° C. for one hour. The reaction solution was then added dropwise into methanol (150 ml) at 0° C., followed by addition of conc. hydrochloric acid (29 ml) and stannous chloride (57 g), for overnight stirring at room temperature. To the resulting solution after concentration was added 12% hydrochloric acid (125 ml), which was then extracted into toluene three times. The organic phase was washed in water and subsequently in a saturated sodium chloride solution and dried over anhydrous magnesium sulfate, to distill off the solvents under reduced pressure. The same procedures as in Example 8 were carried out except for the use of the above residue without purification in place of 2,3-dimethoxyphenol in the step 1 of Example 8, to recover 7,8-dihydroxy-10,11-dihydrodibenz[b,f]thiepin-10-one (Compound 43) represented by the following formula (45) in brown plate crystal.

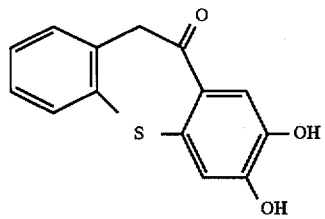

Formula (45)

The Compound 43 has a melting point of 247.0° to 248.5° C. By $^1$H-NMR (90 MHz, DMSO-d$_6$), the Compound 43 has the peaks shown below.

δ(ppm) 4.24 (2H, s, Ar—CH$_2$) 6.98 (1H, s, Ar—H) 7.2–7.8 (4H, m, Ar—H) 7.52 (1H, s, Ar—H)

[EXAMPLE 44]

Production of 10,11-dihydrodibenz[b,f]thiepin-2,3-diol (Compound 44)

The same procedures as in Example 12 were carried out except for the use of 7,8-dimethoxy-10,11-dihydrodibenz[b,f]thiepin-10-one produced in the step 2 of Example 43 as a starting material in the process of Example 12, to recover 10,11-dihydrodibenz[b,f]thiepin-2,3-diol (Compound 44) represented by the following formula (46) in pale pink plate crystal.

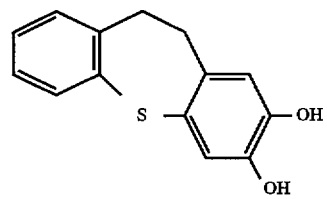

Formula (46)

The Compound 44 has a melting point of 116.4° to 118.4° C. By $^1$H-NMR (90 MHz, CDCl$_3$), the Compound 44 has the peaks shown below.

δ(ppm) 3.2–3.4 (2H, m, CH$_2$) 3.2–3.4 (2H, m, CH$_2$) 6.68 (1H, s, Ar—H) 6.98 (1H, s, Ar—H) 7.0–7.5 (4H, m, Ar—H)

[EXAMPLE 45]

Production of (±)-2,3-dihydroxy-10,11-dihydrodibenz[b,f]thiepin-5-oxide (Compound 45)

10,11-Dihydrodibenz[b,f]thiepin-2,3-diol (100 mg) produced in Example 44 was dissolved in methylene chloride (1 ml), followed by addition of m-chloroperbenzoic acid (100 mg) for stirring at room temperature for 10 minutes. Diluting the solution with ethyl acetate, washing the solution in water and in a saturated sodium chloride solution, drying then the resulting solution over anhydrous magnesium sulfate, the solvents were distilled off under reduced pressure. The residue was purified by silica gel column chromatography (developing solvent: hexane:ethyl acetate=1:2) and recrystallized in hot methanol, to recover ±)-2,3-dihydroxy-10,11-dihydrodibenz[b,f]thiepin-5-oxide (Compound 45) represented by the following formula (47) in mud yellow irregular-shape crystal (90 mg; yield of 38%).

Formula (47)

The Compound 45 has a melting point of 218.4° to 219.9° C. By ¹H-NMR (90 MHz, DMSO-d$_6$), the Compound 45 has the peaks shown below.

δ(ppm) 2.9–3.3 (2H, m, CH$_2$) 2.9–3.3 (2H, m, CH$_2$) 6.63 (1H, s, Ar—H) 7.05 (1H, s, Ar—H) 7.3–7.7 (4H, m, Ar—H) 9.24 (1H, brs, OH) 9.34 (1H, brs, OH)

[EXAMPLE 46]

Production of 2-acetyl-10,11-dihydrodibenz[b,f]oxepin-1,3-diol (Compound 46)

To anhydrous methylene chloride (0.5 ml) were added aluminium chloride (129 mg) and acetyl chloride (69 μl), and the resulting mixture was stirred at room temperature, until no solid was present therein. To the mixture was then added the Compound 12 (0.2 g) produced in Example 12, prior to stirring for another one hour at room temperature. The resulting reaction solution was partitioned with ethyl acetate and dilute hydrochloric acid, and the organic phase was washed in water and in a saturated sodium chloride solution, and dried over anhydrous magnesium sulfate, to distill off the solvents under reduced pressure. The residue was purified by silica gel column chromatography (developing solvent: ethyl acetate:hexane=1:3) and recrystallized in hexane and ethyl acetate, to recover 2-acetyl-10,11-dihydrodibenz[b,f]oxepin-1,3-diol (Compound 46) represented by the following formula (48) in pale yellow needle crystal (0.05 g; yield of 21%).

Formula (48)

The Compound 46 has a melting point of 146.3° to 147.8° C.

The Compound 46 has a melting point of 146.3° to 147.8° C. By ¹H-NMR (90 MHz, CDCl$_3$), the Compound 46 has the peaks shown below.

δ(ppm) 2.69 (3H, s, CH$_3$) 2.8–3.0 (2H, m, CH$_2$) 3.0–3.2 (2H, m, CH$_2$) 6.14 (1H, s, Ar—H) 6.4 (1H, brs, OH) 7.0–7.2 (4H, m, Ar—H) 13.5 (1H, brs, OH)

[EXAMPLE 47]

Production of 4-acetyl-10,11-dihydrodibenz[b,f]oxepin-1,3-diol (Compound 47)

During the purification process by silica gel column chromatography in Example 46, a compound with a slightly higher polarity than that of the Compound 46 was recrystallized in hexane and ethyl acetate, to recover 4-acetyl-10,11-dihydrodibenz[b,f]oxepin-1,3-diol (Compound 47) represented by the following formula (49) in yellow needle crystal.

Formula (49)

The Compound 47 has a melting point of 169.1° to 170.6° C. By ¹H-NMR (90 MHz, CDCl$_3$), the Compound 47 has the peaks shown below.

δ(ppm) 2.90 (3H, s, CH$_3$) 2.9–3.1 (2H, m, CH$_2$) 3.1–3.3 (2H, m, CH$_2$) 6.11 (1H, s, Ar—H) 7.1–7.2 (4H, m, Ar—H)

[EXAMPLE 48]

Production of 4,8-diacetyl-10,11-dihydrodibenz[b,f]oxepin-1,3-diol (Compound 48)

The same procedures as in Example 46 were carried out except for the use of two-equivalents of the reaction reagents to the Compound 12 in the process of Example 46, to recover 4,8-diacetyl-10,11-dihydrodibenz[b,f]oxepin-1,3-diol (Compound 48) represented by the following formula (50) in pale yellow plate crystal.

Formula (50)

The Compound 48 has a melting point of 220.3° to 222.1° C. By ¹H-NMR (90 MHz, DMSO-d$_6$), the Compound 48 has the peaks shown below.

δ(ppm) 2.56 (3H, s, CH$_3$) 2.64 (3H, s, CH$_3$) 2.7–2.9 (2H, m, CH$_2$) 3.0–3.2 (2H, m, CH$_2$) 6.28 (1H, s, Ar—H) 7.26 (1H, d, J=8.1 Hz, Ar—H) 7.7–7.9 (2H, m, Ar—H) 10.9–11.3 (1H, br, OH)

[EXAMPLE 49]

Production of 1-fluoro-7,9-dihydroxy-10,11-dihydrodibenz[b,f]oxepin-10-one (Compound 49)

N,N-Dimethylformamide (20 ml) was added to 2-chloro-6-fluorophenyl acetic acid (3.77 g), 3,5-dimethoxyphenol (3.08 g), potassium carbonate (5.52 g), copper iodide (950 mg) and copper (250 mg), for stirring at 120° C. for 20 hours. The resulting reaction solution was partitioned with ethyl acetate and dilute hydrochloric acid, and the organic phase was washed in water and in a saturated sodium chloride solution, and dried over anhydrous magnesium sulfate, to distill off the solvents under reduced pressure. The residue was purified by silica gel column chromatography (developing solvent: hexane:ethyl acetate=7:3), to recover 2-(3,5-dimethoxyphenoxy)-6-fluorophenyl acetic acid (5.27 g; yield of 86%). By ¹H-NMR (90 MHz, CDCl$_3$), the compound has the peaks shown below.

δ(ppm) 3.72 (3H, s, OCH$_3$) 3.72 (3H, s, OCH$_3$) 3.75 (2H, s, Ar—CH$_2$) 5.8–6.2 (3H, m, Ar—H) 6.5–7.2 (3H, m, Ar—H)

The same procedures as the procedures in and after the step 2 of Example 8 were carried out on the above compound, to recover 1-fluoro-7,9-dihydroxy-10,11-dihydrodibenz[b,f]oxepin-10-one (Compound 49) represented by the following formula (51) in pale yellow needle crystal.

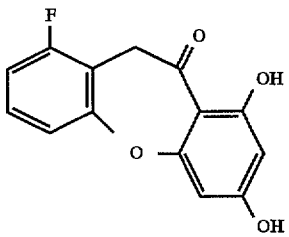

Formula (51)

The Compound 49 has a melting point of 217.9° to 219.4° C. By ¹H-NMR (90 MHz, DMSO-d₆), the Compound 49 has the peaks shown below.

δ(ppm) 4.11 (2H, s, Ar—CH₂) 6.18 (1H, d, J=2.3 Hz, Ar—H) 6.39 (1H, d, J=2.3 Hz, Ar—H) 7.2–7.4 (3H, m, Ar—H) 12.88 (1H, s, OH)

[EXAMPLE 50]

Production of 9-fluoro-10,11-dihydrodibenz[b,f]oxepin-1,3-diol (Compound 50)

The same procedures as in Example 12 were carried out except for the use of 1-fluoro-7,9-dimethoxy-10,11-dihydrodibenz[b,f]oxepin-10-one produced as an intermediate during the process of producing the Compound 49 in Example 49 as a starting material in the process of Example 12, to recover 9-fluoro-10,11-dihydrodibenz[b,f]oxepin-1,3-diol (Compound 50) represented by the following formula (52) in colorless irregular-shape crystal.

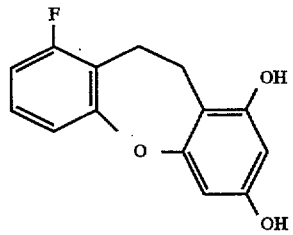

Formula (52)

The Compound 50 has a melting point of 184.9° to 186.0° C. By ¹H-NMR (90 MHz, DMSO-d₆), the Compound 50 has peaks shown below.

δ(ppm) 2.8–3.0 (2H, m, CH₂) 2.8–3.0 (2H, m, CH₂) 6.07 (1H, d, J=2.1 Hz, Ar—H) 6.14 (1H, d, J=2.1 Hz, Ar—H) 6.9–7.3 (3H, m, Ar—H) 9.3–9.5 (1H, br, OH) 9.3–9.5 (1H, br, OH)

[EXAMPLE 51]

Production of 1-fluoro-7,8-dihydroxy-10,11-dihydrodibenz[b,f]oxepin-10-one (Compound 51)

The same procedures as in Example 49 were carried out except for the use of 3,4-dimethoxyphenol in place of 3,5-dimethoxyphenol in the process of Example 49, to recover 1-fluoro-7,8-dihydroxy-10,11-dihydrodibenz[b,f]oxepin-10-one (Compound 51) represented by the following formula (53) in skin-colored needle crystal.

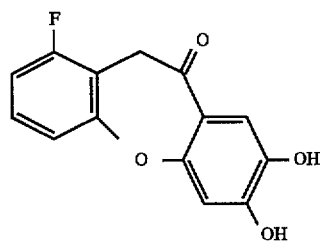

Formula (53)

The Compound 51 has a melting point of 215.4° to 217.4° C. By ¹H-NMR (90 MHz, DMSO-d₆), the Compound 51 has the peaks shown below.

δ(ppm) 4.00 (2H, s, Ar—CH₂) 6.80 (1H, s, Ar—H) 7.0–7.4 (4H, m, Ar—H) 9.7–10.1 (1H, br, OH)

[EXAMPLE 52]

Production of 9-fluoro-10,11-dihydrodibenz[b,f]oxepin-2,3-diol (Compound 52)

The same procedures as in Example 12 were carried out except for the use of 1-fluoro-7,8-dimethoxy-10,11-dihydrodibenz[b,f]oxepin-10-one produced as an intermediate during the process of producing the Compound 51 in Example 51 as a starting material in the process of Example 12, to recover 9-fluoro-10,11-dihydrodibenz[b,f]oxepin-2,3-diol (Compound 52) represented by the following formula (54) in colorless plate crystal.

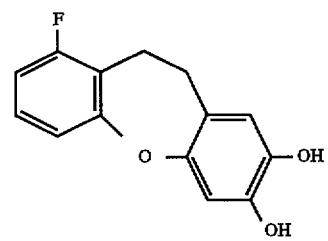

Formula (54)

The Compound 52 has a melting point of 121.3° to 123.3° C. By ¹H-NMR (90 MHz, DMSO-d₆), the Compound 52 has peaks shown below.

δ(ppm) 2.9–3.0 (2H, m, CH₂) 2.9–3.0 (2H, m, CH₂) 6.56 (1H, s, Ar—H) 6.58 (1H, s, Ar—H) 6.8–7.3 (3H, m, Ar—H) 8.7–9.1 (1H, br, OH)

[EXAMPLE 53]

Test of lipid peroxides inhibition

Erythrocyte membrane ghost collected and prepared from rabbits was diluted with phosphate buffer to a protein level of 1 to 2.5 mg/ml, and to 0.85 ml of the diluted solution was added a sample dissolved in 100 μl of dimethyl sulfoxide. The samples were the Compounds 1 to 52 from Examples 1 to 52 and a control antioxidant α-tocopherol. Furthermore, addition of t-butyl hydroperoxide was followed by incubation at 37° C. for 30 minutes.

The level of malonaldehyde generated as a decomposition product of lipid peroxides, was quantitatively determined by the thiobarbiturate method; the concentration (IC₅₀) of a sample capable of suppressing the malonaldehyde level to 50% of the maximum was calculated, to determine the ratio thereof to the IC₅₀ of the control α-tocopherol. The results are shown in the following Table 1.

TABLE 1

| Sample | Effect |
| --- | --- |
| Compound 1 | ± |
| Compound 2 | ++ |
| Compound 3 | + |
| Compound 4 | ++ |
| Compound 5 | ± |
| Compound 6 | ++ |
| Compound 7 | ± |
| Compound 8 | + |
| Compound 9 | ++ |
| Compound 10 | ++ |
| Compound 11 | ± |
| Compound 12 | + |
| Compound 13 | + |
| Compound 14 | + |
| Compound 15 | ± |
| Compound 16 | + |
| Compound 17 | + |
| Compound 18 | + |
| Compound 19 | ± |
| Compound 20 | + |
| Compound 21 | + |
| Compound 22 | + |
| Compound 23 | ± |
| Compound 24 | + |
| Compound 25 | + |
| Compound 26 | + |
| Compound 27 | ± |
| Compound 28 | + |
| Compound 29 | ± |
| Compound 30 | + |
| Compound 31 | + |
| Compound 32 | + |
| Compound 33 | + |
| Compound 34 | ± |
| Compound 35 | + |
| Compound 36 | ± |
| Compound 37 | + |
| Compound 38 | + |
| Compound 39 | + |
| Compound 40 | ++ |
| Compound 41 | ++ |
| Compound 42 | ++ |
| Compound 43 | + |
| Compound 44 | + |
| Compound 45 | + |
| Compound 46 | ± |
| Compound 47 | ± |
| Compound 48 | ± |
| Compound 49 | ± |
| Compound 50 | + |
| Compound 51 | + |
| Compound 52 | + |

Effect:

$\pm: 0.5 \leq \dfrac{IC_{50} \text{ of } \alpha\text{-tocopherol}}{IC_{50} \text{ of Sample}} < 1.5$ $+: 1.5 \leq \dfrac{IC_{50} \text{ of } \alpha\text{-tocopherol}}{IC_{50} \text{ of Sample}} < 2.5$ $++: 2.5 \leq \dfrac{IC_{50} \text{ of } \alpha\text{-tocopherol}}{IC_{50} \text{ of Sample}}$ Industrial Applicability Since the novel tricyclic, condensed heterocyclic compound of the present invention has such as anti-oxidative action, the compound is effective for use in pharmaceutical agents, cosmetics, chemical products and the like.

We claim:

1. A novel anti-oxidative, tricyclic, condensed heterocyclic compound represented by the following formula:

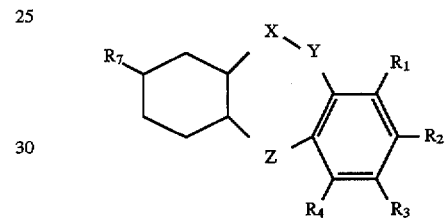

(wherein X—Y represents $CH_2$—C=O provided that X is $CH_2$ and Y is C=O, $CH_2$—$CH_2$ or CH=CH; Z represents O, S, or S=O; $R_1$ to $R_8$ represent independently those selected from the group consisting of hydrogen atom, a hydroxyl group, a halogen group, a lower alkyl group, a lower alkoxyl group, a lower alkyl ketone group and $CF_3$; and at least two of $R_1$ to $R_4$ are hydroxyl groups; and the salts thereof.

* * * * *

UNITED STATES PATENT AND TRADEMARK OFFICE
CERTIFICATE OF CORRECTION

PATENT NO. : 5,734,067
DATED : March 31, 1998
INVENTOR(S) : JINNO et al

It is certified that error appears in the above-indentified patent and that said Letters Patent is hereby corrected as shown below:

The following formula, which appears in the Abstract, at column 1, lines 55-64 and at column 32, lines 25-34:

"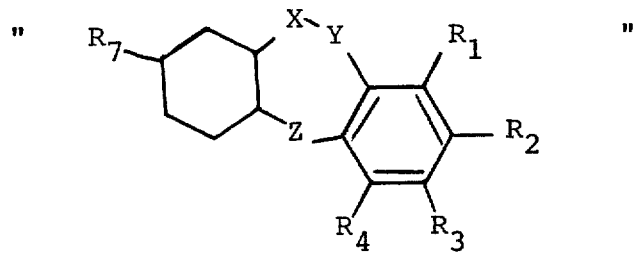"

UNITED STATES PATENT AND TRADEMARK OFFICE
CERTIFICATE OF CORRECTION

PATENT NO. : 5,734,067
DATED : March 31, 1998
INVENTOR(S) : JINNO et al

It is certified that error appears in the above-identified patent and that said Letters Patent is hereby corrected as shown below:

should read, in each instance:

-- 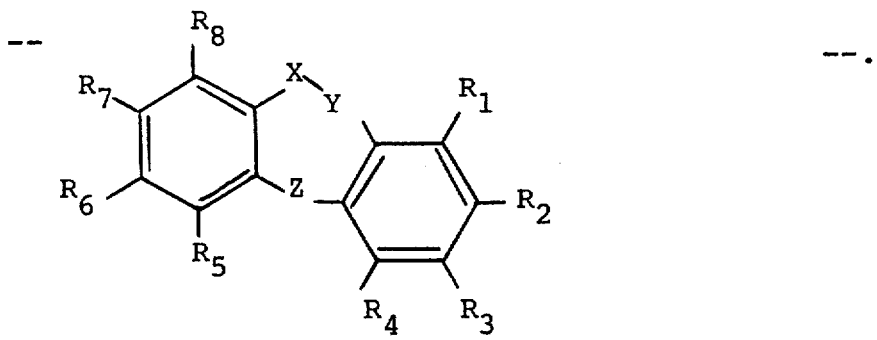 --.

Signed and Sealed this

Seventeenth Day of November, 1998

Attest:

Attesting Officer

BRUCE LEHMAN

Commissioner of Patents and Trademarks